United States Patent [19]
Argento et al.

[11] 4,374,752
[45] Feb. 22, 1983

[54] CATALYST AND PROCESS FOR THE CONVERSION OF METHANOL TO ACETALDEHYDE

[75] Inventors: Benny J. Argento, South Charleston, W. Va.; Wellington E. Walker, deceased, late of Sissonville, W. Va., by Maxine M. Walker, executrix; Rocco A. Fiato, Scotch Plains, N.J.

[73] Assignee: Union Carbide Corporation, Danbury, Conn.

[21] Appl. No.: 279,158

[22] Filed: Jun. 30, 1981

[51] Int. Cl.³ .......................... C07C 45/49; B01J 27/08
[52] U.S. Cl. .................................. 252/429 R; 568/487
[58] Field of Search ..................... 568/487; 252/429 R

[56] References Cited

U.S. PATENT DOCUMENTS

| | | | |
|---|---|---|---|
| 3,091,644 | 5/1963 | Aldridge | 252/429 R |
| 3,356,734 | 12/1967 | Kuraishi | 260/601 |
| 3,625,755 | 6/1972 | Potrafke | 252/429 R |
| 3,681,021 | 8/1972 | Mikovsky | 252/429 R |
| 3,808,246 | 4/1974 | Fahey | 252/429 R X |
| 3,907,890 | 9/1975 | Scanio | 252/429 R |
| 3,944,604 | 3/1976 | Hershman et al. | 252/429 R |
| 3,966,595 | 6/1976 | Gosser | 252/429 R |
| 4,151,208 | 4/1979 | Pretzer et al. | 260/601 R |
| 4,218,340 | 8/1980 | Holmes | 252/429 R |
| 4,225,517 | 9/1980 | Gane | 568/487 |

FOREIGN PATENT DOCUMENTS

| | | | |
|---|---|---|---|
| 10373 | 4/1980 | European Pat. Off. | |
| 11042 | 5/1980 | European Pat. Off. | 568/487 |
| 52-136110 | 11/1977 | Japan | |
| 52-136111 | 11/1977 | Japan | |
| 1546428 | 5/1979 | United Kingdom | |

Primary Examiner—Arthur P. Demers
Attorney, Agent, or Firm—Francis M. Fazio

[57] ABSTRACT

A catalyst mixture is made with improved activity and selectivity to acetaldehyde by using an inert diluent and specifically defined concentrations of cobalt, a halide, a trivalent phosphorus compound, and the inert diluent. Use of the trivalent phosphorus compound significantly inhibits corrosion of the reactor metal.

15 Claims, No Drawings

CATALYST AND PROCESS FOR THE CONVERSION OF METHANOL TO ACETALDEHYDE

BACKGROUND OF THE INVENTION

The present invention relates to a catalyst composition and to the related process for its use in the production of acetaldehyde by the hydroformylation of methanol with carbon monoxide and hydrogen.

The dwindling reserves of crude oil and the uncertainty of availablility of crude oil supplies has led to research for the exploitation of coal, natural gas and other organic materials as the source of organic chemicals traditionally derived from petroleum. It is known that these materials can be used to produce a gas mixture of carbon monoxide and hydrogen known as synthesis gas and that systhesis gas can be used to make methanol, which can be further reacted through homologation and hydroformylation reactions with more synthesis gas in the presence of catalysts to produce other chemicals. Among these other chemicals is acetaldehyde, an organic chemical compound of considerable importance as an intermediate in the production of, for example, ethanol, acetic acid, acetic anhydride, ethyl acetate, butyraldehyde, and butanol as well as other derivatives.

There are various catalyst systems known for use in acetaldehyde-producing processes using the hydroformylation reaction, with many based on cobalt and using a halide promoter. These catalyst systems can be judged on the basis of activity, selectivity, and stability (as defined below). It is desirable that all of these values remain high while minimizing corrosion of the equipment used; however, it is often true that an increase of one of these values will have a detrimental effect on one or more of the others or increase the equipment corrosion. Thus, a catalyst system that displays high values for activity, selectivity, and stability with minimal corrosion would be an improvement over catalysts heretofore disclosed.

"Activity" as used herein denotes the term that relates to the amount of reactants the catalyst can convert per unit volume per unit time. The reactants being carbon monoxide, hydrogen and methanol. The activity can be determined by measuring the rate in which the acetaldehyde product is made. It is important that the reaction be carried out at a sufficiently rapid rate for it to be commercially acceptable.

"Selectivity" as used herein denotes the amount of desired organic products as opposed to other organic by-products formed by the catalyzed reaction. In the production of acetaldehyde, other organic by-products are formed; the main such by-products being ethanol, methyl acetate and methane.

"Stability" as used herein denotes the length of time a catalyst will function before losing its catalytic activity.

"Conversion" as used herein denotes percentage of initially charged methanol converted to acetaldehyde and/or other organic products.

"Realizable acetaldehyde" as used herein denotes the sum of the free acetaldehyde produced plus the amount of acetaldehyde recoverable from 1,1-dimethoxyethane formed during the reaction.

"Corrosion" as used herein denotes the gradual loss of weight or thickness of the materials of construction of the equipment or of the loss of structural integrity of the walls thereof, during the course of the reaction. At the conditions often encountered in carbonylation, hydroformylation and homologation reactions, most halide promoted catalyst systems are corrosive towards metal typically used in these systems leading to an undesirably short life or the need to use expensive materials that do not corrode as readily. It is, therefore, desirable to provide a catalyst system that not only has acceptable activity, selectivity and stability but one that is also less corrosive to the equipment.

The importance of employing catalyst systems containing specifically defined concentrations of components to minimize equipment corrosion and simultaneously enhance activity, selectivity and stability has not heretofore been recognized even though extensive literature exists on the use of halide-promoted, cobalt-based catalysts systems in the carbonylation, hydroformylation, and homologation reactions involving synthesis gas.

Thus, in U.S. Pat. No. 3,356,734 issued to M. Kuraishi et al. on Dec. 5, 1967, there is disclosed a cobalt-iodide catalyst system for the hydroformylation of methanol to produce acetaldehyde. The process, however, exhibits low methanol conversions and low selectivity to acetaldehyde, and there is no recognition indicated of the corrosion problem, nor do they use a phosphorus compound or inert solvent in the reaction.

In U.S. Pat. No. 4,151,208 issued to Pretzer et al. on Apr. 24, 1979, the catalyst system for the production of acetaldehyde is cobalt (II) mesotetraaromaticporphine and an iodine promoter. There is no reference to the use of a phosphorus compound or an inert solvent, nor any mention of the corrosion problem and its resolution.

Japanese Publications No. JA 77/136110 and JA 77/136111 both by Saito et al. and published on Nov. 14, 1977, disclose processes for making aldehydes using catalyst systems containing cobalt, a halogen element and a phosphorus compound. These processes exhibit low selectivity towards acetaldehyde. There is also no recognition of the corrosion problem nor do they disclose the use of an inert solvent in the reaction.

European patent application No. 10,373 by British Petroleum Company Limited and published on Apr. 30, 1980, discloses processes for making ethanol or acetaldehyde using a catalyst system containing cobalt, an iodide or bromide and a polydentate ligand wherein the donor atoms are selected from nitrogen, phosphorus, arsenic, antimony and bismuth. The methanol may be reacted with synthesis gas in the presence of an acid or acid derivative, or an inert liquid which is an aryl halide, a thiophene, a long chain acid or a silicon oil. The predominant product is ethanol when the donor atoms of the polydentate ligand are exclusively nitrogen or phosphorus, particularly phosphorus. The predominant product is acetaldehyde when the donor atoms are exclusively arsenic, antimony or bismuth. There is no reference to the effect of the cobalt and halide catalyst components and the inert diluent nor is there reference to the effect of their relative concentrations on acetaldehyde selectivity or activity. This application teaches away from a catalyst system containing a phosphine and also having high selectivities and activities for acetaldehyde. Particularly, this application shows no appreciation for the necessity of using the entire combination; a source of cobalt, a halide, a phosphorus compound and an inert diluent; at defined concentrations and ratios to obtain high activities and selectivities for acetaldehyde. There is also no teaching nor appreciation of the importance of using a particular class of solvents, those containing oxygen, to direct the reaction to acetaldehyde. There is also no reference to the corrosion problem nor to the effect of the process conditions on the acetaldehyde selectivity and activity for phosphorus-containing catalysts. There is also no mention of the corrosion problem nor its solution.

In British Pat. No. 1,546,428 to Slaugh, published on May 23, 1979 are disclosed catalyst systems similar to those disclosed in the above referenced European Patent Application No. 10,373. Disclosed is a process for the preparation of ethanol by reacting hydrogen and carbon monoxide in the presence of a cobalt catalyst, a hydrocarbon solvent, a halogen ion promoter, and tertiary phosphine. The predominant product is ethanol, generally with significant amounts of other by-products such as acetic acid, methyl acetate and methane. There is no teaching showing the use of oxygen-containing solvents or diluents to obtain high activities and selectivities for acetaldehyde nor is there even disclosed the use of oxygen-containing solvents for any purpose. There is also no recognition of the corrosion problem nor is there any teaching of its solution.

In U.S. Pat. No. 4,225,517, issued Sept. 30, 1980 to Gane is disclosed a process for making acetaldehyde and ethanol. A process for making ethanol is disclosed which uses a catalyst comprising an inert liquid, cobalt, iodide or bromide and a compound containing nitrogen, phosphorus, arsenic, or antimony. In this process, ethanol is the major realizable product. Also disclosed is a process for making acetaldehyde using a system containing cobalt, an iodide or bromide, a compound containing arsenic, antimony or bismuth and various other additives. When triphenylphosphine is used in place of the arsenic, antimony or bismuth compound, ethanol is the major product. There is no disclosure of a phosphorus-containing catalyst that is highly selective to acetaldehyde, nor is there a disclosure that would lead one to such a catalyst. There is also no mention of the corrosion problem nor its solution.

None of the above references suggest or disclose the importance of maintaining particular components of a catalyst system; a source of cobalt, a halide, a phosphorus compound, and an oxygen-containing diluent or solvent; at controlled concentrations and ratios so as to enhance activity, stability and selectivity toward acetaldehyde while simultaneously minimizing equipment corrosion, as is described in the description of our invention below.

SUMMARY OF THE INVENTION

An improved catalyst and process for the hydroformylation reaction of methanol with synthesis gas to produce acetaldehyde has been found. High activity and selectivity to the desired acetaldehyde are possible in a system which is stable and which unexpectedly and unpredictably shows reduced corrosion towards common materials of construction, such as Hastelloy ® B, Hastelloy ® C or 316 stainless steel. The improved process comprises reacting methanol with carbon monoxide and hydrogen in the presence of a catalyst system comprising a source of cobalt, a source of a halide, a trivalent phosphorus containing compound and an inert diluent wherein the relative concentrations of catalyst system components and methanol are maintained within specifically and critically defined ranges as explained below.

The catalyst and process of this invention show unusually high selectivity for the production of realizable acetaldehyde in a completely unexpected system, one containing a phosphorus compound. It was unexpected and unpredictable that the phosphorus containing system of this invention would be selective to the production of acetaldehyde since British Pat. No. 1,546,428, U.S. Pat. No. 4,225,517 and E.P.A. No. 10,373, discussed above, all teach that such systems are selective to ethanol. It has now been found that a catalyst system containing trivalent phosphorus compounds and used with an inert diluent or cosolvent, provides for a catalyst system that is highly selective toward acetaldehyde and that has excellent activity and stability. It has also been unexpectedly found that the use of a phosphorus compound significantly inhibits corrosion of the equipment without deleterious effects on the catalyst activity or realizable acetaldehyde selectivity; in some instances improved activities and selectivities were noted.

DESCRIPTION OF THE INVENTION

This invention is the improved catalyst system discussed above and its use in the hydroformylation reaction of methanol with synthesis gas to selectively produce acetaldehyde under conditions such that there are experienced stability, activity, efficiency and corrosion benefits not heretofore achievable.

The catalyst system contains four important components that are present at specifically defined concentrations and is employed under the reaction conditions stated, all as more fully described and defined below. There are present (a) a source of cobalt, (b) a source of a halide, (c) a trivalent phosphorus compound and (d) an inert oxygen-containing diluent. The catalyst system must contain an inert diluent or solvent to obtain the improved results of the invention. The advantages as above stated, in particular the improved selectivity and activity towards acetaldehyde and the improved corrosion properties are obtainable by using the components of the catalyst, the cobalt, the halide, the phosphorus compound and the inert diluent, in the specifically defined concentrations and ratios. The diluent must be an oxygen-containing compound.

The cobalt component of the catalyst can come from a number of sources such as any of the known cobalt carboxylates, for example, cobalt formate, cobalt acetate, cobalt propionate, cobalt butyrate, cobalt benzoate, cobalt valerate, cobalt hexanoate, and the like; the known cobalt carbonyl compounds such as dicobalt octacarbonyl, cobalt tetracarbonyl hydride, compounds formed in situ such as methyl cobalt tetracarbonyl, acetyl cobalt tetracarbonyl, and the like, or the phosphine and/or halide substituted analogs of any of the above, many of which are known to those skilled in the art; cobalt oxide and cobalt hydroxide; cobalt carbonate and cobalt bicarbonate; the soluble cobalt halides such as cobalt iodide, cobalt bromide and cobalt chloride; and cobalt. Cobalt may also be supplied as a supported form such as on a silica, alumina, or polystyrene support or on any one of the supports known in the art. Cobalt silicate, cobalt titanate, and cobalt orthotitanate and the like are also suitable sources of cobalt. A convenient source of cobalt is cobalt (II) acetate tetrahydrate.

The halide component can be any halide except fluoride. Preferably the halide is bromide or iodide, most preferably iodide. If iodide, the halide can be supplied iodine or any of its derivatives. Illustrative of suitable compounds one can mention, acetyl iodide, potassium iodide, sodium iodide, lithium iodide, calcium iodide, ammonium iodide, methyl ammonium iodide, tetraethyl ammonium iodide, methyl ammonium iodide, tetramethyl ammonium iodide, triphenylphosphonium iodide, tricyclohexylphosphonium iodide, cobalt iodide; hydrogen iodide; the alkyl iodides having from 1 to 10 carbon atoms such as methyl iodide, ethyl iodide, propyl iodide, 2-ethylhexyl iodide, n-decyl iodide, or any other source of iodide which will ionize to form iodide ions in the reaction medium. One can also employ any other organic compound that will furnish iodide to the reaction medium. Further, one can use mixtures of iodine and/or iodide compounds, if so desired.

The trivalent phosphorus compounds are the phosphines of the formula:

PR$_3$ and the polydentate phosphines of the formula:

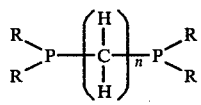

wherein each R group taken individually is similar or different, and is; (a) a saturated or unsaturated, linear or branched alkyl group having from 1 to 20 carbon atoms, preferably 4 to 10 carbon atoms (b) an aryl, aralkyl, or alkaryl group having from 6 to 10 ring carbon atoms, preferably 6 ring carbon atoms; or (c) a saturated or unsaturated cycloalkyl having from 5 to 8 ring carbon atoms preferably 5 to 6 ring carbon atoms or (d) when two such R groups are attached to the same phosphorus atom and taken together, they are a saturated or unsaturated divalent alkylene group having from 4 to 10 carbon atoms preferably 4 to 6 carbon atoms; and n is an integer having a value of 2 to 10, preferably from 2 to 6. Any of the known phosphorus compounds can be used and illustrative thereof one can mention triethylphosphine, tributylphosphine, triphenylphosphine, tri-(4-methoxyphenyl)phosphine, tri-p-tolylphosphine, tris(3-chlorophenyl)phosphine, diphenylhexylphosphine, dimethyl(3-methoxyphenyl) phosphine, dibutylstearylphosphine, tribenzylphosphine, cyclohexyldibutylphosphine, tricyclohexylphosphine, propyl diphenylphosphine, dipropyl phenylphosphine, ethyl dipropylphosphine, bis(diphenylphospino) ethane, bis(diethylphosphino)propane, bis(disphenylphosphino)butane and the like. The phosphine compounds can also contain substituents that do not unduly interfere with the reaction.

Any inert diluent which contains oxygen and is not unduly reactive with the other constitutents in the reaction system and which does not unduly interfere with the reaction can be used. Also any oxygen-containing diluent that may react in the system but forms products that do not unduly interfere with the reaction is suitable. Among the diluents for use in the invention are the polyalkylene glycols, excepting di-ethylene glycol, that have from 2 to 350 ethyleneoxy or propyleneoxy units or mixtures of such units in the molecule and are liquid under reaction conditions, the alkyl or aryl or cycloalkyl monoethers or di-ethers of the polyalkylene glycols having from 2 to 350 ethyleneoxy or propyleneoxy units or mixture of such units in the molecule as well as the mono-ethers or di-ethers of ethylene glycol or propylene glycol, 1,4-dioxane, sulfolane, tripropylphosphine oxide, and methyl acetate. Also suitable are primary alcohols such as ethanol, n-propanol, n-butanol, isobutanol, n-pentanol, and n-hexanol; secondary alcohols such as isopropanol, 2-pentanol and 3-pentanol; cyclic alcohols such as cyclopentanol, polyols such as 1,4-butanediol, 2,5-hexanediol and polytetramethylene ether glycol (Polymeg 1000 (trademark)); ketones such as acetone, methyl ethyl ketone, 2,5-hexanedione, cyclopentanone, and cyclohexanone; ethers such as diethylether, tetrahydrofuran, 2,5-dimethyltetrahydrofuran and diphenyl ether. Also suitable are mixtures of two or more of the above. Water can also be used as a diluent in small amounts or in a mixture with one or more of the above. A high volume of water can lead to undesirable by-products; therefore, the system preferably contains a small amount of water. About 10 volume percent of water in the total reaction system has been found suitable. About 75 volume percent of water has been found unsuitable. Since water is a reaction by-product in the formation of acetaldehyde, water is likely to be present in the reaction system in any case, particularly when the continuous reaction mode is used. Some other compounds, like water, cannot be used in a high volume but can be in a mixture or in a small amount in the catalyst system. These include ethylene glycol, 1,4-butane diol, 2,4-pentane dione, diethylene glycol, N-methyl pyrolidinone, propylene glycol and tripropylphosphine oxide. The above list of suitable diluents is not to be considered all inclusive since any known suitable inert diluent or solvent can be used possessing the characteristics discussed above. Usually the preferred inert diluents or solvents are those which form monophase systems and are essentially unreactive during the reaction.

In the practice of the invention the concentrations and ratios of the constituents of the catalyst system are as follows:

(1) The volume ratio of inert solvent or diluent to methanol charged should be from 0.3:1 to 20:1 preferably from 0.5:1 to 8:1.

(2) The cobalt is present at a concentration of from 1 to 40 milligram-atoms of cobalt per gram-mole of methanol charged, preferably from 3 to 15 milligram-atoms per gram-mole of methanol.

(3) The halide is present at a halide to cobalt milligram-atom ratio of 1:1 to 10:1, preferably greater than 2:1 and most preferably from 2:1 to 6:1.

(4) The phosphorus compound is present such that the phosphorus to halide milligram-atom ratio is from 0.1:1 to 2.8:1, preferably from 0.4:1 to 2:1.

As previously indicated unexpectedly improved results are achieved when specifically defined concentrations and ratios are employed in the catalyst system. Ethanol is not primarily produced as is disclosed in the above discussed British Pat. No. 1,546,428, U.S. Pat. No. 4,225,517 and E.P.A. No. 10,373, but rather unexpectedly acetaldehyde is selectively produced as the predominant product, in a system containing a trivalent phosphorus compound in the specified ratios. These surprising results are obtained by carefully controlling the composition of the catalyst system. It has been found that the combined effect of maintaining the catalyst constituents within the above defined ratios provides significantly improved performance, with selectivity to realizable acetaldehyde higher than that reported in the prior art discussed above.

The improved selectivities and activities of the invention are also improved by preferably maintaining the process conditions in defined ranges discussed below; i.e. the mole ratio of hydrogen to carbon monoxide in the synthesis gas and the temperature, and the pressure.

Therefore, in the acetaldehyde forming process of the invention, the mole ratio of hydrogen to carbon monoxide in the synthesis gas, or other synthesis gas-forming compositions used, is generally from 0.2:1 to 10:1, preferably from 0.25:1 to 5:1, most preferably from 0.5:1 to 1.5:1.

The reaction is generally carried out at a temperature of from about 120° C. to 250° C., preferably from about 160° C. to 225° C.

The pressure used is generally from 1,000 psig to 10,000 psig, preferably from 1,500 psig to 6,000 psig.

Further, it has also been observed that corrosion of the equipment was diminished to an unexpected and unpredictable extent. This is due in large part to the use of the phosphorus compound, in the catalyst system contained in the defined amounts. The discovery that corrosion is reduced under these conditions is of significant importance in view of the costs involved in erecting a new facility and in replacing corroded parts.

The improved results of the invention are not due to one factor alone but due to the combined effect of the defined catalyst composition i.e. the cobalt concentration, the halide to cobalt milligram-atom ratio and the phosphorus to halide milligram-atom ratio, the inert diluent present in the defined amount; and also in part to the process conditions as defined, i.e., the hydrogen to carbon monoxide molar ratio, the temperature and pressure.

In a typical practice of the invention on a laboratory scale, the autoclave is cleaned, the liquid reactants, catalyst compounds and diluents are charged into the autoclave after which the solid components are charged, the reactor is closed, purged with synthesis gas and then pressurized with synthesis gas. With agitation the pressurized contents are heated to the desired temperature and then additional synthesis gas is added to the desired pressure plus 250 psig. The reaction is permitted to proceed until sufficient gas has reacted such that the pressure has fallen 250 psig below the desired pressure. The reaction is then repressurized to the desired pressure plus 250 psig and the reaction continued. One such cycle is considered 500 psig gas uptake. The cycles are continued for a set period of time or until the desired gas uptake (generally about 3,000 psig) has occurred. It is generally undesirable to continue the reaction for a excessively long time, since with long reaction times condensation products of higher molecular weight form as impurities. In laboratory batch reactions, reaction times of from 5 minutes to 4 hours have been found suitable. At the conclusion of the reaction, the reactor contents are cooled and the vapor phase is analyzed and vented. The liquid contents of the reactor are then removed and analyzed.

The following examples serve to further illustrate the invention.

In the batch procedure used in the examples below, prior to charging the catalyst, diluent, and methanol, the laboratory autoclave reactor was washed with methanol at 100° C. at from 400 to 1,000 psig synthesis gas pressure for 30 minutes. The reactor was drained, opened, rinsed with acetone, and dried with nitrogen. To the open and cleaned reactor there were charged first the liquid and then the solid components. The reactor was closed, purged with synthesis gas and then pressured to about 3,000 psig with synthesis gas. With agitation (about 750 rpm), the reactor contents were heated to the indicated temperature over a period of about 45 minutes whereby the pressure increased. When the temperature had been reached, the reactor was brought to the desired pressure plus about 250 psig with synthesis gas. The reaction was allowed to consume gas until the pressure had fallen to about 250 psig below the desired pressure. The reactor was then repressurized. One such cycle was considered a 500 psig synthesis gas uptake. Unless otherwise specified, reactions were allowed to proceed until the indicated psig gas uptake had occurred. The operating pressure reported in the examples was the desired pressure for the run. At the end of an experiment, the reactor contents were normally cooled to 10° C. A vapor phase sample was taken and analyzed for CO, $H_2$, $CO_2$, and $CH_4$ plus other gaseous components using gas-liquid chromatography. The reactor gas phase was then vented through two dry ice-acetone traps. The reaction was pressurized three times with 90 psig nitrogen and vented through the same trap system.

The liquid reactor contents were dumped into a chilled pressure bottle and crown capped and analyzed. To analyze the liquid phase samples a Hewlett-Packard Model 5880 gas chromatograph was employed having two columns, ⅛ inch by 20 feet in size and packed with 60/80 mesh Chromosorb 101 ® (a polyvinyl styrene). Each column was made from two 10 ft lengths connected in series with a ⅛ inch union.

Values for selectivity and rate of production are for realizable acetaldehyde or in other words the figures also include 1,1-dimethoxyethane, commonly known as dimethyl acetal, on a contained acetaldehyde basis. Dimethyl acetal is formed as a result of the acetaldehyde product combining with methanol in the reactant mixture and is readily converted back to acetaldehyde and methanol.

The selectivity values are calculated by dividing the weight of acetaldehyde by the total weight of reaction products. Included in the weight of acetaldehyde is dimethyl acetal on a contained acetaldehyde basis. Values for rate of production of acetaldehyde also include dimethyl acetal on a contained acetaldehyde basis.

EXAMPLE I

A series of expirements was carried out as described above with a gas uptake of 3,000 psig. and a reactor pressure of 5,000 psig (±250 psig). The initial charge to the reactor consisted of 112.5 ml of the diethylether of diethylene glycol, 37.5 ml of methanol, 8 mmol of cobalt acetate tetrahydrate, 14 mmol of iodine and, 30.8 mmol of triphenylphosphine. The temperature, and hydrogen to carbon monoxide molar ratio are shown in Table I. The results of these experiments are also shown in Table I. The selectivities are in weight percent and the product rate in g.mol/l/h. Selectivity and rate for realizable acetaldehyde includes the sum of acetaldehyde and dimethyl acetal on a contained acetaldehyde basis. The realizable acetaldehyde production rate and selectivity are significantly higher than those found in the prior art. Also the rates and selectivities of ethanol and other by-products are much smaller than those found in the prior art. This example demonstrates how through practice of the invention, a product comprising predominately realizable acetaldehyde is made with only small amounts of ethanol and other by-products.

TABLE I

| Run | H$_2$/CO | Temp | Selectivity (Weight Percent) | | | | | | Rate (g.mol/1/hr) | | |
| --- | --- | --- | --- | --- | --- | --- | --- | --- | --- | --- | --- |
| | | | AcH | DMA | Rel. AcH | EtOH | MeOAc | CH$_4$ | Rel. AcH | EtOH | CH$_4$ |
| 1 | 1.5 | 170 | 69.9 | 20.4 | 89.3 | 1.9 | 6.3 | 1.4 | 4.9 | 0.11 | 0.24 |
| 2 | 1.5 | 190 | 71.5 | 18.1 | 88.0 | 0.2 | 4.4 | 3.1 | 6.5 | 0.21 | 0.68 |
| 3 | 1.5 | 205 | 70.3 | 16.6 | 84.0 | 4.2 | 2.7 | 6.1 | 6.3 | 0.32 | 1.35 |
| 4 | 1.0 | 205 | 74.5 | 11.1 | 84.0 | 3.7 | 6.4 | 4.2 | 10.2 | 0.45 | 1.46 |

AcH = Acetaldehyde
DMA = Dimethyl Acetal
Rel. AcH = Realizable Acetaldehyde
EtOH = Ethyl Alcohol
MeOAc = Methyl Acetate

EXAMPLE II

A series of experiments was carried out as described above at a temperature of 170° C., a gas uptake of 3,000 psig, a reactor pressure of 5000 psig (±250 psig) and a H$_2$/CO molar ratio of 1.5:1. The initial charge to the reactor consisted of 112.5 ml of the diethylether of diethylene glycol, 37.5 ml. of methanol, 4 mmol of cobalt acetate tetrahydrate and 7 mmol of iodine. The specific phosphorus compound used in each run and its quantity are shown in Table II. Also shown for realizable acetaldehyde are the weight percent selectivity and the production rate as gram moles per liter per hour. The realizable acetaldehyde is the sum of the free acetaldehyde produced plus the amount of acetaldehyde recoverable from the dimethyl acetal formed during the reaction. In Run 11 the source of the phosphorus component was polystyrene containing 6.2 weight percent triphenylphosphine bound thereto, the amount used was sufficient to provide 2.95 milligram-atoms phosphorus to the reaction. For the various phosphorus-containing additives the results show a very favorable activity for acetaldehyde as shown by the production rate of acetaldehyde.

TABLE II

| | | | Realizable Acetaldehyde | |
| --- | --- | --- | --- | --- |
| Run | R$_3$P(mmol) | Ph$_2$P(CH$_2$)PPh$_2$ (mmol) | Selectivity (wt %) | Production Rate (g.mol/1/hr) |
| 1 | R = phenyl (7.7) | — | 81.6 | 2.1 |
| 2 | R = p-tolyl (7.7) | — | 73.5 | 1.9 |
| 3 | R = cyclohexyl(7.7) | — | 88.0 | 2.8 |
| 4 | — | n = 2(3.85) | 78.8 | 1.7 |
| 5 | — | n = 2(7.7) | 85.4 | 1.6 |
| 6 | — | n = 3(3.85) | 87.4 | 1.6 |
| 7 | — | n = 4(3.85) | 77.3 | 1.9 |
| 8 | — | n = 5(3.85) | 79.2 | 2.2 |
| 9 | — | n = 6(3.85) | 78.1 | 1.9 |
| 10 | R = phenyl (3.85) | n = 2(1.925) | 77.0 | 2.2 |
| 11 | R = phenyl | — | 72.2 | 2.2 |

Ph = phenyl

EXAMPLE III

A series of experiments using various diluents (runs 1-11) was carried out as described above at a temperature of 170° C., a reactor pressure of 5000 psig (±250 psig) and a H$_2$/CO molar ratio of 1.5:1. The initial charge to the reactor consisted of 112.5 ml. of the diluent, 37.5 ml. of methanol, 4 mmol of cobalt acetate tetrahydrate, 9.0 mmol of iodine, and 19.8 mmol of triphenylphosphine. The specific diluent used in each run, its quantity, and the gas uptake are shown in Table III as are the weight percent selectivity for realizable acetaldehyde and also the rate of production of realizable acetaldehyde as gram moles per liter per hour.

In run 11 there was 4.0 mmol cobalt acetate tetrahydrate, 14.0 mmol iodine, and 30.8 mmol triphenyl phosphine. The other conditions were as in the previous runs.

On runs 2, 3, and 8 diluents were used that should not be used in large amounts; therefore, the high rates and selectivities characteristic of the practice of the invention are not shown in these runs. The other runs show how one can obtain the high selectivities and activities possible by practice of the invention.

TABLE III

| | | Realizable Acetaldehyde | | |
| --- | --- | --- | --- | --- |
| Run | Diluent | Wt. Percent Selectivity | Production Rate (g. mol/ 1/h) | Gas Uptake (psig) |
| 1 | DEDEG | 90.6 | 4.00 | 3000 |
| 2 | Tripropylphosphine oxide | 45.5 | 0.12 | 900 |
| 3 | N-methyl pyrolidinone | 25.7 | 0.10 | 2250 |
| 4 | 1.2-Dimethoxybenzene | 73.7 | 3.40 | 3000 |
| 5 | 18-Crown-6 Ether | 79.8 | 1.00 | 3000 |
| 6 | Diphenyl Ether | 90.5 | 1.60 | 3000 |
| 7 | Sulfolane | 70.2 | 1.00 | 3000 |
| 8 | Diethylene Glycol | 29.5 | 0.11 | 3000 |
| 9 | Triethylene Glycol | 66.7 | 1.10 | 3000 |
| 10 | 2-Methyl Pentanediol-2,4 | 65.6 | 0.27 | 3500 |
| 11 | DBDEG | 89.0 | 2.7 | 3000 |

DEDEG = Diethylether of diethylene glycol
DBDEG = Dibutyl ether of diethylene glycol

EXAMPLE IV

A series of experiments was carried out as described above using various diluents at a temperature of 170° C., a reactor pressure of 5000 psig (±250 psig), a H$_2$/CO molar ratio of 1.5:1 and with 3000 psig gas uptake. The initial charge to the reactor consisted of 120 ml. of the diluent, 30.0 ml. of methanol, 4 mmol of cobalt acetate tetrahydrate, 8 mmol of iodine and 8 mmol of triphenyl phosphine. The specific diluent used in each run is shown in Table IV as are the weight percent selectivity for realizable acetaldehyde, the production rate of realizable acetaldehyde as gram mole per liter per hour, and the reaction time. The mixture of run 4 was 90 ml methyl acetate, 6-ml ethyl acetate, 12-ml n-propanol, and 6-ml n-butanol. All the runs shown good selectivity and rate for realizable acetaldehyde for the different diluents used.

TABLE IV

| Run | Diluent | Acetaldehyde Production Rate (g.mole/1/h) | Wt. Percent Selectivity Acetaldehyde | Reaction Time (h) |
| --- | --- | --- | --- | --- |
| 1 | DMEG | 1.37 | 89.4 | 1.1 |
| 2 | DMDEG | 2.97 | 68.5 | 0.7 |
| 3 | Methyl Acetate | 0.6 | 68.5 | 2.0 |

TABLE IV-continued

| Run | Diluent | Acetaldehyde Production Rate (g.mole/l/h) | Wt. Percent Selectivity Acetaldehyde | Reaction Time (h) |
|---|---|---|---|---|
| 4 | Mixture | 0.63 | 80.9 | 1.8 |
| 5 | DMTEG | 4.1 | 84.2 | 0.8 |

DMEG = Dimethyl ether of ethylene glycol
DMDEG = Dimethyl ether of diethylene glycol
DMTEG = Dimethyl ether of tetraethylene glycol

EXAMPLE V

This example shows how an oxygen-containing diluent may be used to increase the acetaldehyde selectivity to a surprisingly high extent. A series of experiments was carried out as described at 5000 psig (±250 psig); 8 mmol of cobalt acetate tetrahydrate and 16 mmol of iodine were in the initial charge for runs 1 to 4. For runs 1 to 2 there was no diluent and 150 ml of methanol only was used in the initial charge to the reactor, in runs 3 and 4 112.5 ml. of 1,4-dioxane and, 37.5 ml. of methanol were used. The weight percent selectivity for realizable acetaldehyde, the production rate of realizable acetaldehyde as gram moles per liter per hour, the reaction time, and gas uptake are shown in Table V. The results indicate that the use of a diluent can increase both the activity and selectivity of the catalyst system to acetaldehyde.

TABLE V

| Run | $H_2$:CO Molar Ratio | Uptake (psig) | Realizable Acetaldehyde Production Rate (g.mole/l/h) | Wt. Percent Selectivity | Reaction Time (h) |
|---|---|---|---|---|---|
| 1* | 1.5 | 4750 | 0.48 | 43.9 | 4.0 |
| 2* | 2.5 | 2650 | 0.35 | 44.7 | 6.0 |
| 3+ | 1.5 | 4000 | 2.14 | 87.4 | 1.3 |
| 4+ | 2.5 | 2500 | 1.52 | 82.6 | 1.2 |

*no diluent used
+diluent used

EXAMPLE VI

A series of experiments at various $I^-$/Co and $P/I^-$ gram-atom ratios was carried out at a temperature of 170° C., a pressure of 5,000 psig (±250 psig) and a $H_2$/CO molar ratio of 1.5:1. The initial charge to the reactor contained 112.5 ml. of the diethylether of diethylene glycol, 37.5 ml of methanol, and 4 mmol of cobalt acetate tetrahydrate. The iodide was supplied as iodine and the phosphorus as triphenylphosphine. The gas uptake was 3,000 psig except run 16 which was 880 psig. In Table VI there are shown the reaction time, the selectivity in weight percent of realizable acetaldehyde and the production rate for realizable acetaldehyde in gram-moles per liter per hour for various $I^-$/Co and $P/I^-$ ratios. The outcome of these experiments show that at these ranges of $I^-$/Co and $P/I^-$ milligram-atom ratios within the scope of the invention result in a high rate and selectivity. Comparison of runs 4-8 runs at various phosphorus to halide gram-atom ratios with runs 17 to 18 run under similar conditions but with no phosphorus compound shows how use of a phosphorus compound can increase both activity as shown by the production rate and also selectivity towards acetaldehyde. A completely surprising result, since as discussed above, the prior art teaches that ethanol is the predominant product when phosphorus compounds are used. The data also shows acceptable production rate and selectivity to acetaldehyde at various halide to cobalt milligram-atom ratios and phosphorus to halide milligram-atom ratios.

TABLE VI

| Run | $I^-$/Co mg-atom ratio | $P/I^-$ mg-atom ratio | Realizable Acetaldehyde Production Rate (g.mol/l/h) | Wt. Percent Selectivity | Reaction Time (h) |
|---|---|---|---|---|---|
| 1 | 2.5 | 0.55 | 2.2 | 77.6 | 0.97 |
| 2 | 2.5 | 1.1 | 2.9 | 87.7 | 1.03 |
| 3 | 2.5 | 1.5 | 2.4 | 87.0 | 1.32 |
| 4 | 2.5 | 1.9 | 2.0 | 90.9 | 1.4 |
| 5 | 3.5 | 0.55 | 2.8 | 80.2 | 0.95 |
| 6 | 3.5 | 1.1 | 3.5 | 93.8 | 0.92 |
| 7 | 3.5 | 1.5 | 3.0 | 92.2 | 1.0 |
| 8 | 3.5 | 1.9 | 1.8 | 88.5 | 1.72 |
| 9 | 4.5 | 0.55 | 3.6 | 84.4 | 0.87 |
| 10 | 4.5 | 1.1 | 4.1 | 87.7 | 0.85 |
| 11 | 4.5 | 1.5 | 2.8 | 80.8 | 1.03 |
| 12 | 4.5 | 1.9 | 1.4 | 91.2 | 1.8 |
| 13 | 5.5 | 0.55 | 3.3 | 86.4 | 0.97 |
| 14 | 5.5 | 1.1 | 3.4 | 88.7 | 0.87 |
| 15 | 5.5 | 1.5 | 3.0 | 87.0 | 0.97 |
| 16 | 5.5 | 1.9 | 0.3 | 88.2 | 4.0 |
| 17 | 3.5 | 0 | 1.7 | 70.3 | 1.3 |
| 18 | 3.5 | 0 | 1.5 | 71.1 | 1.2 |

EXAMPLE VII

A series of experiments at various $P/I^-$ ratios was carried out at a temperature of 170° C., a pressure of 5,000 psig (±250 psig), a gas uptake of 3000 psig and a $H_2$/CO mole ratio of 1.5:1. The initial charge to the reactor contained 112.5 ml of the diethylether of diethylene glycol, and 37.5 ml of methanol with 4.0 mmol of cobalt supplied as cobalt acetate tetrahydrate. The iodide was supplied as iodine and the phosphorus as tricyclohexyphosphine. Production rate and selectivity of realizable acetaldehyde are shown in Table VII for various phosphorus to iodide gram-atom ratios. The results shown the unexpected and surprisingly high selectivity towards acetaldehyde obtainable through practice of the invention.

TABLE VII

| Run | $I^-$/Co mg-atom ratio | $P/I^-$ mg-atom ratio | Realizable Acetaldehyde Production Rate (g.mol/l/h) | Wt. Percent Selectivity | Reaction Time (h) |
|---|---|---|---|---|---|
| 1 | 3.5 | 0.55 | 1.2 | 83.8 | 1.93 |
| 2 | 3.5 | 1.1 | 1.5 | 83.9 | 2.03 |
| 3 | 3.5 | 1.5 | 1.2 | 80.4 | 2.33 |
| 4 | 3.5 | 1.9 | 0.76 | 76.9 | 3.18 |

EXAMPLE VIII

A series of experiments at various $P/I^-$ ratios was carried out at a temperature of 170° C., a pressure of 5,000 psig (±250 psig) and a $H_2$/CO ratio of 1.5:1. The gas uptake was 3,000 psig except for run 5 which was 3080 psig. The initial charge to the reactor contained 112.5 ml of 1,4-dioxane, and 37.5 ml of methanol with 4.0 mmol of cobalt supplied as cobalt acetate tetrahydrate. The iodide was supplied as iodine and the phosphorus as triphenyl phosphine. Production rate and selectivity of realizable acetaldehyde are shown in Table VII for various phosphorus to iodide gram-atom ratios.

Comparison of phosphorus-free run 1 showing a low selectivity to acetaldehyde with the other runs showing the high selectivity obtainable by practice of the invention using a phosphorus compound shows how the selectivity to acetaldehyde is substantially increased using a phosphorus compound in the catalyst system.

TABLE VIII

| Run | $I^-/Co$ mg-atom ratio | $P/I^-$ mg-atom ratio | Realizable Acetaldehyde | | Reaction Time (h) |
| | | | Production Rate (g.mol/1/h) | Wt. Percent Selectivity | |
|---|---|---|---|---|---|
| 1 | 3.5 | 0 | 0.54 | 58.5 | 2.50 |
| 2 | 3.5 | 0.55 | 2.2 | 82.9 | 1.32 |
| 3 | 3.5 | 1.1 | 2.1 | 86.1 | 1.52 |
| 4 | 3.5 | 1.5 | 1.6 | 82.2 | 1.95 |
| 5 | 3.5 | 1.9 | 0.43 | 76.2 | 4.0 |

EXAMPLE IX

A series of experiments at various Co concentrations and $I^-/Co$ and $P/I^-$ ratios was carried out at a temperature of 170° C., a pressure of 5,000 psig ($\pm$250 psig), a gas uptake of 3000 psig and a $H_2/CO$ mole ratio of 1.5:1. In the initial charge to the reactor there were 112.5 ml of the diethylether of diethylene glycol and 37.5 ml of methanol and 4.0 mmol of cobalt supplied as cobalt acetate tetrahydrate. The iodide was supplied as iodine and the phorphorus as triphenylphosphine. Production rate and selectivity of realizable acetaldehyde as shown in Table IX for various amounts and ratios of cobalt, iodide and phosphorus. Some of these runs are operated in the non-preferred ranges of the I/CO and $P/I^-$ milligram-atom ratios and thus do not show the highest selectivity and activity obtainable by practice of the invention. However comparison of these runs with run 4 with $I^-/CO$ milligram-atom ratio outside of the scope of the invention will show either a higher production rate or a higher selectivity of realizable acetaldehyde for the runs without the scope of the invention.

TABLE IX

| Run | Cobalt Acetate Tetrahydrate (mmol) | I/Co mg-atom ratio | $P/I^-$ mg-atom ratio | Realizable Acetaldehyde | |
| | | | | Wt. Percent Selectivity | Production Rate (g.mol/1/h) |
|---|---|---|---|---|---|
| 1 | 4.0 | 5.5 | 1.9 | 0.35 | 73.7 |
| 2 | 4.0 | 7.0 | 1.5 | 0.39 | 72.2 |
| 3 | 4.0 | 9.5 | 1.1 | 1.0 | 69.8 |
| 4 | 4.0 | 19.1 | 0.55 | 0.45 | 49.5 |
| 5 | 4.0 | 2.5 | 2.3 | 0.59 | 73.9 |
| 6 | 4.0 | 2.5 | 2.7 | 0.10 | 60.2 |
| 7 | 4.0 | 3.5 | 2.3 | 0.21 | 68.1 |
| 8 | 4.0 | 3.5 | 2.7 | 0.10 | 60.9 |
| 9 | 3.0 | 2.0 | 0.4 | 0.75 | 58.9 |
| 10 | 3.0 | 2.0 | 2.0 | 0.87 | 73.9 |
| 11 | 3.0 | 1.0 | 0.4 | 0.58 | 61.0 |
| 12 | 3.0 | 1.0 | 2.0 | 1.27 | 70.8 |
| 13 | 15 | 2.0 | 0.4 | 1.90 | 85.1 |
| 14 | 15 | 2.0 | 2.0 | 2.90 | 65.3 |
| 15 | 15 | 1.0 | 0.4 | 1.74 | 51.6 |
| 16 | 15 | 1.0 | 2.0 | 2.0 | 60.2 |

EXAMPLE X

This example illustrates the superior anticorrosion properties of the catalyst of the invention.

A first series (I) of eight phosphine-free experiments was run at a temperature of 140° C., a pressure of 4,000 psig ($\pm$250 psig) and at a $H_2/CO$ molar ratio of 1.2:1. The combined volume of the methanol and the diluent was 150 ml. Table X summarizes the conditions of each of these runs.

A second series (II) of eight companion experiments was conducted at the same conditions as the first series using the same initial reactor charges except that triphenylphosphine was incorporated in the charge to give a phosphorus to iodide milligram atom ratio of 0.50. Corrosion test coupons of metal compositions typical of high pressure reactors used in reactions of this type were placed in the high pressure reactor during each of the eight runs of each series.

TABLE X

| Run | Cobalt Acetate Tetrahydrate (mg) | Iodine (mmol) | Methanol (ml) | Diluent |
|---|---|---|---|---|
| 1 | 1.0 | 1.0 | 30 | 1,4 dioxane |
| 2 | 1.0 | 4.0 | 30 | 1,4 dioxane |
| 3 | 1.0 | 5.0 | 30 | 1,4 dioxane |
| 4 | 1.0 | 20.0 | 30 | 1,4 dioxane |
| 5 | 4.0 | 1.0 | 75 | DMTEG |
| 6 | 4.0 | 4.0 | 75 | DMTEG |
| 7 | 4.0 | 5.0 | 75 | DMTEG |
| 8 | 4.0 | 20.0 | 75 | DMTEG |

DMTEG = Dimethyl ether of tetraethylene glycol.

The average corrosion rates were determined by loss of thickness of the coupons and thereby calculating the annual rate of loss of the thickness.

| | Coupon Metal Series | Corrosion Rate (inches/yr) | |
| | | Hastelloy B ® | Hastelloy C ® |
|---|---|---|---|
| (I) | Phosphine Free | 0.0670 | 0.0390 |
| (II) | Phosphine Added | 0.005 | 0.008 |

These standard corrosion rate analyses indicate that the catalyst mixtures containing the phosphine compounds, as disclosed in the present invention, are significantly less corrosive to these metals than are the comparable phosphine free catalyst mixtures.

The same compositions in previous examples are shown here as having superior anti-corrosion properties. Thus is demonstrated how one by practice of this invention can achieve high activity and selectivity for acetaldehyde and yet provide for lower corrosion rates.

Tests were also run using corrosion test coupons of 316 stainless steel. The results of these tests showed much lower corrosion rates than is normal in halide promoted systems. This is significant since it is well known that halide promoted cobalt catalysts are very corrosive to 316 stainless steel and for this reason 316 stainless steel has, heretofore, been an unacceptable material for process equipment used in halide-promoted catalyst systems. However, through practice of the instant invention corrosion of this and other materials is significantly reduced to a point allowing substantial economic benefit.

The data in the above examples shows the surprisingly high activity, and selectivity to realizable acetaldehyde and the improved corrosion properties observed when using the phosphine-containing catalyst compositions of the present invention.

What is claimed is:

1. A catalyst system for the production of acetaldehyde by the reaction of methanol, carbon monoxide and hydrogen, which catalyst comprises (I) a source of cobalt, (II) a source of iodide or bromide, (III) an inert oxygen-containing diluent, and (IV) a trivalent phosphorus compound of the formula:

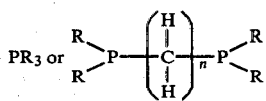

wherein each R group taken individually is similar or different, and is; (a) a saturated or unsaturated, linear or branched alkyl group having from 1 to 20 carbon atoms, or (b) an aryl, aralkyl, or alkaryl group having from 6 to 10 ring carbon atoms, or (c) a saturated or unsaturated cycloalkyl having from 5 to 8 ring carbon atoms, or (d) when two such R groups are attached to the same phosphorus atom and taken together, a saturated or unsaturated divalent alkyl group having from 4 to 10 carbon atoms; and wherein n is an integer from 2 to 10, and wherein the inert diluent to methanol volume ratio is from 0.3:1 to 20:1, the cobalt concentration is from 1 to 40 milligram-atoms of cobalt per gram-mole of methanol charged, the halide to cobalt milligram-atom ratio is from 1:1 to 10:1; and the phosphorus to halide milligram-atom ratio is from 0.1:1 to 2.8:1.

2. The catalyst of claim 1 wherein each R group taken individually is similar or different, and is; (a) a saturated or unsaturated, linear or branched alkyl group having from 4 to 10 carbon atoms (b) an aryl, aralkyl, or alkaryl group having 6 ring carbon atoms, or (c) a saturated or unsaturated cycloalkyl having from 5 to 6 ring carbon atoms, or, (d) when two such R groups are attached to the same phosphorus atom and taken together, a saturated or unsaturated divalent alkylene group having from 4 to 10 carbon atoms; and wherein n is an integer from 2 to 6.

3. The catalyst of claim 1 wherein the diluent to methanol volume ratio is from 0.5:1 to 8.1, the cobalt concentration is from 3 to 15 milligram-atoms of cobalt per mole of methanol charged, the iodide or bromide to cobalt milligram-atom ratio is from 2:1 to 10:1, and the phosphorus to halide milligram-atom ratio is from 0.4:1 to 2:1.

4. The catalyst of claim 3 wherein the iodide or bromide to cobalt milligram-atom ratio is from 2:1 to 6:1.

5. The catalyst of claim 1 wherein the trivalent phosphorus compound is triphenylphosphine.

6. The catalyst of claim 1 wherein the trivalent phosphorus compound is tricyclohexylphosphine.

7. A process for the production of acetaldehyde by the reaction of methanol, carbon monoxide and hydrogen wherein the reaction is catalyzed by cobalt and an iodide or bromide promoter in the presence of an inert oxygen-containing diluent and a trivalent phosphorus compound of the formula:

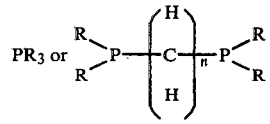

wherein each R group taken individually is similar or different, and is; (a) a saturated or unsaturated, linear or branched alkyl group having from 1 to 20 carbon atoms, (b) an aryl, aralkyl, or alkaryl group having from 6 to 10 ring carbon atoms, or (c) a saturated or unsaturated cycloalkyl having from 5 to 8 ring carbon atoms, or (d), when two such R groups are attached to the same phosphorus atom and taken together a saturated or unsaturated divalent alkylene group having from 4 to 10 carbon atoms; and wherein n is an integer from 2 to 10, the diluent to methanol volume ratio is from 0.3:1, to 20:1, the cobalt concentration is from 1 to 40 milligram-atoms of cobalt per gram-mole of methanol charged, the halide to cobalt milligram-atom ratio is from 1:1 to 10:1, and the phosphorus to halide milligram-atom ratio is from 0.1:1 to 2.8:1, the hydrogen to carbon monoxide mole ratio is from 0.2:1 to 10.1.

8. The process of claim 7 wherein each R group taken individually is similar or different, and is a (a) a saturated or unsaturated, linear or branched alkyl group having from 4 to 10 carbon atoms (b) an aryl, aralkyl, or alkaryl group having 6 ring carbon atoms, or (c) a saturated or unsaturated cycloalkyl having from 5 to 6 carbon atoms, or (d), when two such R groups are attached to the same phosphorus atom and taken together, a saturated or unsaturated divalent alkylene group having from 4 to 10 carbon atoms; and wherein n is an integer from 2 to 6.

9. The process of claim 7 wherein the diluent to methanol volume ratio is from 0.5:1 to 8.1 cobalt concentration is from 3 to 15 milligram-atoms of cobalt per gram-mole of methanol charged, the iodide or bromide to cobalt milligram-atom ratio is from 2:1 to 10:1 the phosphorus to halide milligram-atom ratio is from 0.4:1 to 2:1.

10. The process of claim 9 wherein the iodide or bromide to cobalt milligram-atom ratio is from 2:1 to 6:1.

11. The process of claim 7 wherein the trivalent phosphorus compound is triphenylphosphine.

12. The process of claim 7 wherein the trivalent phosphorus compound is tricyclohexylphosphine.

13. The process of claim 7 wherein the hydrogen to carbon monoxide mole ratio is from 0.2:1 to 10:1, the temperature is 120° C. to 250° C. and the pressure is from 1,000 psig to 10,000 psig.

14. The process of claim 13 wherein the hydrogen to carbon monoxide mole ratio is from 0.25:1 to 5:1, the temperature is from 160° C. to 225° C. and the pressure is from 1,500 psig to 6,000 psig.

15. The process of claim 14 wherein the hydrogen to carbon monoxide mole ratio is from 0.5:1 to 1.5:1.

* * * * *

UNITED STATES PATENT AND TRADEMARK OFFICE
CERTIFICATE OF CORRECTION

PATENT NO. : 4,374,752
DATED : 2-28-83
INVENTOR(S) : B.J. Argento, W.E. Walker, R.A. Fiato It is certified that error appears in the above—identified patent and that said Letters Patent is hereby corrected as shown below:

Column 13, in Table IX the values for Run 10, in the five columns used to report the data, should read as follows to correspond to the original specification

| RUN | COLUMN | | | | |
|-----|-----|-----|-----|-----|-----|
|  | 1 | 2 | 3 | 4 | 5 |
| 10 | 3.0 | 2.0 | 2.0 | 0.87 | 73.9 |

Signed and Sealed this

Twenty-sixth Day of April 1983

[SEAL]

Attest:

GERALD J. MOSSINGHOFF

Attesting Officer   Commissioner of Patents and Trademarks

UNITED STATES PATENT AND TRADEMARK OFFICE
CERTIFICATE OF CORRECTION

PATENT NO. : 4,374,752
DATED : 2/28/83
INVENTOR(S) : B. J. Argento, W. E. Walker, R. A. Fiato It is certified that error appears in the above—identified patent and that said Letters Patent is hereby corrected as shown below:

Column 13, Table IX, the headings at the tops of the last two columns should be interchanged so that the fifth heading becomes the last heading and the last heading becomes the fifth heading in the Table; they will appear in the following order:

| Production Rate (g.mol/l/h) | Wt. Percent Selectivity |
|---|---|

Signed and Sealed this

Twenty-sixth Day of July 1983.

[SEAL]

Attest:

GERALD J. MOSSINGHOFF

Attesting Officer    Commissioner of Patents and Trademarks